US011529799B2

(12) United States Patent
Angeli et al.

(10) Patent No.: US 11,529,799 B2
(45) Date of Patent: Dec. 20, 2022

(54) METHOD FOR THE PRODUCTION OF AN ELASTIC LAMINATE AND LAMINATED ELASTIC PRODUCT

(71) Applicant: PANTEX INTERNATIONAL S.P.A., Sulmona (IT)

(72) Inventors: Pietro Angeli, Pescara (IT); Antonio Caira, Sulmona (IT); Carmine Di Benedetto, Sulmona (IT); Gianluigi Fornoni, Brusaporto (IT)

(73) Assignee: PANTEX INTERNATIONAL S.P.A., Sulmona (IT)

( * ) Notice: Subject to any disclaimer, the term of this patent is extended or adjusted under 35 U.S.C. 154(b) by 754 days.

(21) Appl. No.: 15/756,461

(22) PCT Filed: Aug. 30, 2016

(86) PCT No.: PCT/IB2016/055167
§ 371 (c)(1),
(2) Date: Feb. 28, 2018

(87) PCT Pub. No.: WO2017/037617
PCT Pub. Date: Mar. 9, 2017

(65) Prior Publication Data
US 2018/0345641 A1 Dec. 6, 2018

(30) Foreign Application Priority Data
Sep. 1, 2015 (IT) .......................... UB2015A003333

(51) Int. Cl.
*B29C 37/00* (2006.01)
*B32B 37/00* (2006.01)
(Continued)

(52) U.S. Cl.
CPC .... *B32B 37/0084* (2013.01); *A61F 13/15699* (2013.01); *B29C 48/0018* (2019.02);
(Continued)

(58) Field of Classification Search
CPC ...... B32B 37/0076–0084; B29C 65/18; B29C 43/24
See application file for complete search history.

(56) References Cited

U.S. PATENT DOCUMENTS

| 2003/0105446 A1* | 6/2003 | Hutson | B32B 7/02 |
| | | | 604/385.22 |
| 2007/0144660 A1* | 6/2007 | O'Sickey | B29C 66/83415 |
| | | | 156/229 |
| 2012/0328849 A1* | 12/2012 | Neill | B32B 3/08 |
| | | | 428/195.1 |

FOREIGN PATENT DOCUMENTS

WO     2008/085983 A2     7/2008

* cited by examiner

*Primary Examiner* — Matthew J Daniels
*Assistant Examiner* — Andrew L Swanson
(74) *Attorney, Agent, or Firm* — McGlew and Tuttle, P.C.

(57) ABSTRACT

A method for the production of an elastic laminate, comprising the following steps in a same production line: to coextrude a first web of elastic film (F) with at least three layers (F1, F2, F1), comprising at least two different polymer materials, to feed contemporaneously said coextruded first elastic film (F) web and two second nonwoven webs (T1, T2) to a thermal, binding calender (14), wherein the first elastic film web is arranged between said two second nonwoven webs when entering the calender; wherein said first elastic film web, during the movement from the coextrusion step to the thermal binding step, passes from a melted state, in the coextrusion step, to a solidified and cold state when entering the calender, to join, through spot welding in said calender, said second nonwoven webs with respective opposite outer layers of said first elastic film web, thus producing an intermediate web (P1), to stretch mechanically said intermediate web according to a direction transverse to the same web.

16 Claims, 3 Drawing Sheets

(51) Int. Cl.
| | | |
|---|---|---|
| *B32B 7/05* | (2019.01) | |
| *B29C 48/08* | (2019.01) | |
| *B29C 48/00* | (2019.01) | |
| *B29C 48/21* | (2019.01) | |
| *B29C 65/00* | (2006.01) | |
| *B29C 65/18* | (2006.01) | |
| *B32B 37/08* | (2006.01) | |
| *B29C 48/92* | (2019.01) | |
| *A61F 13/15* | (2006.01) | |
| *B32B 3/26* | (2006.01) | |
| *B32B 5/02* | (2006.01) | |
| *B32B 25/10* | (2006.01) | |
| *B32B 27/12* | (2006.01) | |
| *B32B 27/32* | (2006.01) | |
| *B32B 37/02* | (2006.01) | |
| *B32B 38/00* | (2006.01) | |
| *B32B 37/20* | (2006.01) | |
| *B32B 38/06* | (2006.01) | |
| *B32B 37/14* | (2006.01) | |
| *B32B 37/15* | (2006.01) | |
| *B29L 7/00* | (2006.01) | |
| *B29L 9/00* | (2006.01) | |
| *B29L 31/48* | (2006.01) | |

(52) U.S. Cl.
CPC .......... *B29C 48/0021* (2019.02); *B29C 48/08* (2019.02); *B29C 48/21* (2019.02); *B29C 48/92* (2019.02); *B29C 65/18* (2013.01); *B29C 66/0244* (2013.01); *B29C 66/0342* (2013.01); *B29C 66/1122* (2013.01); *B29C 66/21* (2013.01); *B29C 66/45* (2013.01); *B29C 66/712* (2013.01); *B29C 66/723* (2013.01); *B29C 66/7294* (2013.01); *B29C 66/81433* (2013.01); *B29C 66/83413* (2013.01); *B32B 3/266* (2013.01); *B32B 5/022* (2013.01); *B32B 7/05* (2019.01); *B32B 25/10* (2013.01); *B32B 27/12* (2013.01); *B32B 27/32* (2013.01); *B32B 37/02* (2013.01); *B32B 37/08* (2013.01); *B29C 66/71* (2013.01); *B29C 66/919* (2013.01); *B29C 66/929* (2013.01); *B29C 2948/92704* (2019.02); *B29C 2948/92942* (2019.02); *B29L 2007/00* (2013.01); *B29L 2009/00* (2013.01); *B29L 2031/4878* (2013.01); *B32B 37/0053* (2013.01); *B32B 37/14* (2013.01); *B32B 37/15* (2013.01); *B32B 37/203* (2013.01); *B32B 37/206* (2013.01); *B32B 38/06* (2013.01); *B32B 2038/0028* (2013.01); *B32B 2307/51* (2013.01); *B32B 2307/54* (2013.01); *B32B 2309/02* (2013.01); *B32B 2555/02* (2013.01)

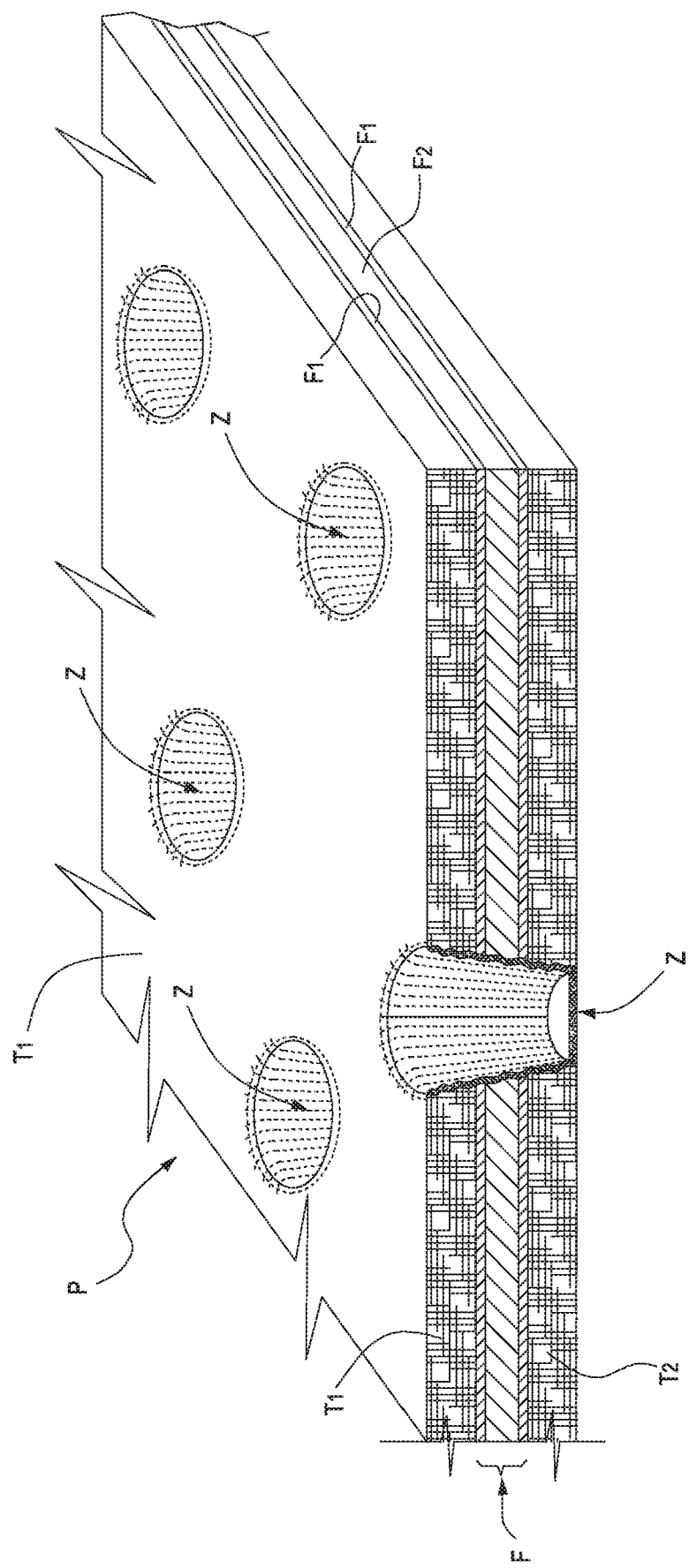

FIG. 3

| | ABS | ABS/PA | ASA | COC | MABS | PA 12 | PA 612 | PA 6 | PA 6-3-T | PA PACM 12 | PA 66 | PBT | PBT/ASA | PC | PE-HD | PE-LD | PEEK | PES | PMMA | POM | PP | PPS | PPSU | PS | PSU | PFTE | SAN | TPE |
|---|---|---|---|---|---|---|---|---|---|---|---|---|---|---|---|---|---|---|---|---|---|---|---|---|---|---|---|---|
| ABS | X | | X | | X | | | | | | | X | X | X | | | | X | X | X | | | | | X | | X | X |
| ABS/PA | X | X | X | | | | X | | | | X | X | X | | | | | X | | | | | | | X | | X | |
| ASA | X | | X | | | | | | | | | X | X | | | | | | | | | | | | | | X | |
| COC | | | | X | | | | | | | | | | | | | | | X | | | | | | | | | |
| MABS | X | | | | X | | | | | | | | | | | | | | | | | | | | | | | |
| PA 12 | | | | | | X | X | X | X | X | X | | | | | | | | | X | | | | | | | | |
| PA 612 | | | | | | X | X | X | X | X | | | | | | | | | | | | | | | | | | |
| PA 6 | | | | | | X | X | X | X | X | X | | | | X | X | | | X | | | | | X | | | | |
| PA 6-3-T | | | | | | X | X | X | X | X | X | | | | | | | | | X | | | | | | | | |
| PA PACM 12 | | | | | | X | X | X | X | X | X | | | | | | | | | | | | | | | | | |
| PA 66 | | | | | | X | X | X | | X | | | | | X | X | | | X | | | | | X | | | | X |
| PBT | X | X | | | | X | X | | | | | X | | X | X | | | X | | | | | | | X | | X | |
| PBT/ASA | X | | | | | | | | | | | | | | X | | | X | | | | | | | X | | | |
| PC | X | | | | | | | X | | | | X | X | X | | | | X | | | | | | | | | X | X |
| PE-HD | | | | | | | | X | | | X | | | X | X | | | | X | X | | | | | | | | |
| PE-LD | | | | | | | | X | | X | | | | X | X | | | | X | X | X | | | | | | | |
| PEEK | | | | | | | | | | | | | | | | | X | | | | | | | | | | | |
| PES | X | | | | | | | | | | | X | X | | | | | X | X | | | | | | X | | | |
| PMMA | X | | | X | | | | | | | | X | | X | X | | | X | X | X | | | | X | | | X | |
| POM | X | | | | | | | X | | | | | | X | X | X | X | X | | | | | | | | | | |
| PP | | | | | | | | X | | | X | | | | X | X | X | | | | | | | | | | | X |
| PPS | | | | | | | | X | X | X | | X | | | X | | X | | X | | | | | | X | | | |
| PPSU | | | | | | | | | | | | | | | | | | | | | | | X | | | | | |
| PS | | | | | | | | X | | | X | | | X | X | | | | X | | | | | X | | | X | |
| PSU | X | | | | | | | | | | | X | X | | | | | X | | | | | | | X | | | |
| PFTE | | | | | | | | | | | | | | | | | | | | | | | | | | X | | |
| SAN | X | | X | | | | | | | | | X | | X | | | | X | | | | | | X | | | X | |
| TPE | | | | | | | | | | | | X | | X | | | | | X | | | | | | | | | X |

METHOD FOR THE PRODUCTION OF AN ELASTIC LAMINATE AND LAMINATED ELASTIC PRODUCT

TECHNICAL FIELD

The present invention relates to flexible elastic sheets or, more generally, laminates, comprising elastic films joined with nonwovens, to be used, for example, in hygienic and sanitary products, etc., like closures or parts of diapers, panty liners, and other products.

More in particular, the object of the invention is a method for the production of an elastic laminate and a laminated elastic product produced by means of said method.

State of the Art

As it is well known, hygienic and sanitary products, such as diapers, bandages, paper napkins, disposable clothes etc. have required, for a long time, high technical and "sensorial" performances.

This kind of products often requires optimal elastic features, for instance in order to be used to realize closures or other portions of baby diapers.

These products shall be not only able to elongate, but also provided with adequate tensile strength, even after a certain number of cycles.

Another important aspect is that these products shall be pleasant to the touch, for instance soft, in correspondence of the interface between product and user contact area.

At the same time, they shall ensure adequate strength during use and a particularly light and non "invasive" look.

The products currently available on the market are not able to satisfy all these requirement at the same time; above all, they are not able to ensure adequate softness, elasticity and strength at the same time.

OBJECT AND SUMMARY OF THE INVENTION

The main object of the present invention is to provide a production method allowing to produce an elastic laminate, especially, but without limitation, for hygienic and sanitary products etc., having high elasticity, high tensile strength and increased softness with respect to the known products.

This and other objects, which will be better explained below, are achieved by means of a method for the production of an elastic laminate, comprising the following steps in a same production line:

to coextrude a first web of elastic film with at least three layers, comprising at least two different polymer materials, to feed contemporaneously said coextruded first elastic film web and two second nonwoven webs to a thermal binding calender, wherein the first elastic film web is arranged between said two second nonwoven webs when entering the calender; wherein said first elastic film web, during the movement from the coextrusion step to the thermal binding step, passes from a melted state, in the coextrusion step, to a solidified and cold state when entering the calender, to join, through spot welding in said calender, said second nonwoven webs with respective opposite outer layers of said first elastic film web, thus producing an intermediate web, to stretch mechanically said intermediate web according to a direction transverse to the same web.

The production line provides for the continuous feeding of the three webs, from a starting area up to a collection area downstream of the stretching area.

As well known, the web feeding direction, or at least the feeding direction of the intermediate web after the calender, is called MD-Machine direction, whilst the direction transverse to MD is called CD-Cross Direction.

Therefore, the webs are preferably fed continuously along the line, or at least through the calender.

Once the intermediate web has been stretched, it can be cut into portions of the desired length, that can be wound and stored.

Welding spots or areas means regions or areas of discrete dimensions, formed due to the effect of heat and pressure exerted by protuberances provided on a calender roller. Shape and dimensions of the welding spots or areas are similar or derive from the shape and dimensions of the protuberance vertexes. They may be, for instance, round or oval, or may have irregular shape, like "islands", i.e. welding areas surrounded by non-welding areas. The regions or areas may have equal shape and/or dimensions, or they may have different shape and/or dimensions, or they may have partially equal shape and/or dimensions.

The calender is preferably equipped with two rollers: one is a flat contrast roller, the other is provided with protuberances forming the discrete welding spots or areas.

For the mechanical stretching step in CD a station is for example provided, comprising two cylinders, which are arranged above each other, between which the web passes and which are provided with rings equally spaced from one another; the rings of one cylinder enter the spaces between the rings of the other cylinder, thus transversally stretching the intermediate web that has been laminated in the calender.

The coextruded elastic film has preferably a temperature, when entering the calender, equal to, or lower than, 1/7 of the temperature the elastic film has at the end of the coextrusion step; this temperature is preferably lower than 1/10; at the end of the coextrusion step, the elastic film has a temperature preferably comprised between 220° C. and 270° C., while, when entering the calender, said coextruded elastic film has a temperature preferably comprised between 10° C. and 40° C., and more preferably between 15° C. and 35° C.

Preferably, after the extrusion step and before the joining step, i.e. before entering the calender, the film passes through a cooling station, for example a pair of cooling rollers, in order to achieve a temperature similar to the temperature it has when entering the calender, i.e. a temperature comprised between 10° C. and 40° C., and more preferably between 15° C. and 35° C.

The cooling contributes to structure the elastic film adequately, so that, thanks to the lamination in the calender and the subsequent stretching step, the final laminate is particularly elastic, resistant and soft.

In order to facilitate the cooling, the first web of coextruded elastic film may adequately travel, from the extrusion step to the entrance into the calender, an air path comprised between 5 m and 20 m, and more preferably comprised between 8 m and 13 m, at ambient temperature.

Preferably, before the stretching step and after the heat-welding step the intermediate web may be cooled up to a temperature comprised between 15° C. and 40° C., for example by means of a pair of known cooling rollers.

Preferably, the elastic film comprises exactly three layers, wherein the ratio between the sum of the thicknesses of the two outer layers and the thickness of the inner layer of the coextruded elastic film entering the calender is comprised between 1/3 and 1/25 and more preferably between 1/7 and 1/21.

The thickness of the elastic film is preferably comprised between 0.04 mm and 0.14 mm.

These ratios allows to achieve, for example, optimal performance in terms of elasticity and strength, ensuring at the same time the required softness of the final laminate.

Adequately, the two outer layers of the elastic film may be made of the same polymer material and preferably have the same thickness.

One or more layers of the elastic film are preferably made of one or more of the following materials: elastomers: poly (ethylene-butene), poly (ethylene-hexene), poly (ethylene-octene), poly (ethylene-propylene), poly (styrene-butadiene-styrene), poly (styrene-isoprene-styrene), poly (styrene-ethylene-butylene-styrene), poly (ester-ether), poly (ether-amide), poly (ethylene-vinyl acetate), poly (ethylene-methyl acrylate), poly (ethylene-acrylic acid), poly (ethylene butyl acrylate), polyurethane, poly (ethylene-propylene-diene), ethylene-propylene rubber.

One or more layers of the elastic film may be also made of polymers similar to rubber, for example polymers made of polyolefins produced by single-site catalysts.

One or more layers of the elastic film may be also made of polymers produced by means of known catalysts, for example metallocene catalysts; for example, ethylene, propylene and other olefins may be polymerized with butene, hexene, octene etc. in order to obtain elastomers like poly (ethylene-butene), poly (ethylene-hexene), poly (ethylene-octene), poly (ethylene-propylene) and/or polyolefin terpolymers thereof, suitable for one or more layers of the elastic film.

one or more layers of the elastic film may be made of polyolefin elastomers, such as Dow® Infuse™, ExxonMobile®, Vistamaxx®, and the like; and/or a combination thereof or other adequate elastic material.

According to preferred embodiments, the second nonwoven webs have substantially equal dimensions and composition.

In the present description, the term "fibers" generically means both fibers, short or long, and filaments.

Preferably, at least one of the second nonwoven webs (and preferably both the webs) is a spun bound web.

Moreover, one or more second webs may be carded, heat-sealable and extendible.

According to preferred embodiments, at least part of the materials forming the outer layers of the elastic film are thermally compatible with at least part of the materials forming the fibers of the nonwoven web they respectively face.

Thermal compatibility means the ability of two materials to remain joined together after heat-welding, or to remain joined together when they are thermally fused above each other and then cooled. For example, FIG. 3 shows a table with a matrix, wherein in the columns and in the rows some materials are indicated, and X indicates that the material in the row and the material in the column are thermally compatible.

Preferably, at least one nonwoven web (and preferably both the webs) has a thickness, before entering the calender, comprised between 0.1 mm and 0.6 mm, and more preferably between 0.15 mm and 0.5 mm.

In this description, the thickness has been measured according to EDANA WSP 120.6.

Preferably, at least one nonwoven web (and preferably both the webs) has a weight, before entering the calender, comprised between 10 and 40 $g/m^2$, measured according to EDANA WSP 130.1.

The nonwovens are preferably extendible and non-elastic. This means that, when subjected to traction, they can elongate, but do not have an elastic behavior.

According to preferred embodiments, the temperature of the calender rollers is comprised between 120° C. and 160° C.

Preferably, the lamination pressure between the calender rollers is comprised between 50 $kg/cm^2$ and 200 $kg/cm^2$.

The final thickness of the laminated product P at the end of processing is preferably comprised between 0.4 mm and 2 mm, and more preferably between 0.5 mm and 1.5 mm.

The weight of the laminated product P, at the end of processing, is preferably comprised between 50 and 140 $g/m^2$.

According to preferred embodiments, the thickness of the laminated product exiting the production line has an increased thickness with respect to the sum of the single nonwoven webs and the elastic film entering the calender, and this increment is comprised between 50% and 66%.

According to preferred embodiments:
  the ratio between MD elongation at break at 10N and laminate thickness after the stretching step is lower than 8, and preferably lower than 7.5, and/or
  the ratio in (N/50 mm)/(mm), between CD tensile strength and laminate thickness after the stretching step is lower than 79, and preferably lower than 78, and/or
  the ratio in ($g/m^2$/mm) between laminate weight and thickness after the stretching step is lower than 105, and more preferably lower than 100.

The MD elongation has been measured according to EDANA WSP 110.4; the tensile strength has been measured according to EDANA WSP 110.4, with the only exception of the specimen, that, instead of having a dimension of 50×80 mm, was an isosceles trapezoid with the smaller base equal to 55 mm, the longer base equal to 95 mm and the height equal to 80 mm; the grammage has been measured according to EDANA WSP 130.1; the thickness has been measured according to EDANA WSP 120.6.

According to preferred embodiments, the welding spot or welding area density is comprised between 15 and 60 spots/$cm^2$.

Preferably, the welding spots or areas are distributed on the whole area of the laminated product homogeneously and/or uniformly.

A further object of the present invention is an elastic laminate, to be especially used, but without limitation, for hygienic and sanitary products etc., for instance closures for diapers, having high elasticity, high tensile strength and increased softness with respect to known products; the elastic laminate comprises:
  a polymer intermediate elastic film formed by three coextruded layers, wherein the outer layers are made of the same polymer material, and the inner layer is made of a different polymer material,
  two nonwoven fabrics joined, through spot or area welding, to respective outer layers of the coextruded elastic film;
and wherein
  the ratio between MD elongation at break at 10N and laminate thickness after the stretching step is lower than 8, and preferably lower than 7.5, and/or the ratio in (N/50 mm)/(mm), between CD tensile strength and laminate thickness after the stretching step is lower than 79, and preferably lower than 78, and/or the ratio in (g/m²/mm) between laminate weight and thickness after the stretching step is lower than 105, and more preferably lower than 100.

As above, the MD elongation has been measured according to EDANA WSP 110.4; the tensile strength has been measured according to EDANA WSP 110.4, with the only exception of the specimen, that, instead of having a dimension of 50×80 mm, was an isosceles trapezoid with the smaller base equal to 55 mm, the longer base equal to 95 mm and the height equal to 80 mm; the grammage has been measured according to EDANA WSP 130.1; the thickness has been measured according to EDANA WSP 120.6.

Preferably, the welding spot or welding area density is comprised between 15 and 60 spots/cm².

The thickness of the laminated product P is preferably comprised between 0.5 mm and 1.5 mm.

The weight of the laminated product P, at the end of processing, is preferably comprised between 60 and 140 g/m².

One or more layers of the elastic film are preferably made of one or more of the following materials: elastomers: poly (ethylene-butene), poly (ethylene-hexene), poly (ethylene-octene), poly (ethylene-propylene), poly (styrene-butadiene-styrene), poly (styrene-isoprene-styrene), poly (styrene-ethylene-butylene-styrene), poly (ester-ether), poly (ether-amide), poly (ethylene-vinyl acetate), poly (ethylene-methyl acrylate), poly (ethylene-acrylic acid), poly (ethylene butyl acrylate), polyurethane, poly (ethylene-propylene-diene), ethylene-propylene rubber.

One or more layers of the elastic film may be also made of polymers similar to rubber, for example polymers made of polyolefins produced by single-site catalysts.

One or more layers of the elastic film may be also made of polymers produced by means of known catalysts, for example metallocene catalysts; for example, ethylene, propylene and other olefins may be polymerized with butene, hexene, octene etc. in order to obtain elastomers like poly (ethylene-butene), poly (ethylene-hexene), poly (ethylene-octene), poly (ethylene-propylene) and/or polyolefin terpolymers thereof, suitable for one or more layers of the elastic film.

one or more layers of the elastic film may be made of polyolefin elastomers, such as Dow® Infuse™, ExxonMobile®, Vistamaxx®, and the like; and/or a combination thereof or other adequate elastic material.

Preferably, the second nonwoven webs have substantially equal dimensions and composition.

Preferably, at least one of the second nonwoven webs (and preferably both the nonwoven webs) has bicomponent fibers, preferably of the coaxial type. The bicomponent fibers preferably comprise PP and PE. Preferably, at least one of the second nonwoven webs (and preferably both the webs) is a spun bound web.

One or more of the second webs may be made of monofilament fiber, for example polypropylene, and may be a spun bound web.

Moreover, one or more of the second webs may be carded, heat-sealable and extendible.

According to preferred embodiments, at least part of the materials forming the outer layers of the elastic film are thermally compatible with at least part of the materials forming the fibers of the nonwoven web with which it is into contact.

BRIEF DESCRIPTION OF THE DRAWINGS

Further characteristics and advantages of the present invention will be more apparent from the description of a preferred, although not exclusive, embodiment, illustrated by way of non-limiting example in the attached tables of drawings, wherein:

FIG. 2 is a schematic cross section of a laminated product according to the invention;

FIG. 3 is a table showing the thermal compatibility of materials.

DETAILED DESCRIPTION OF AN EMBODIMENT OF THE INVENTION

Figure 1:
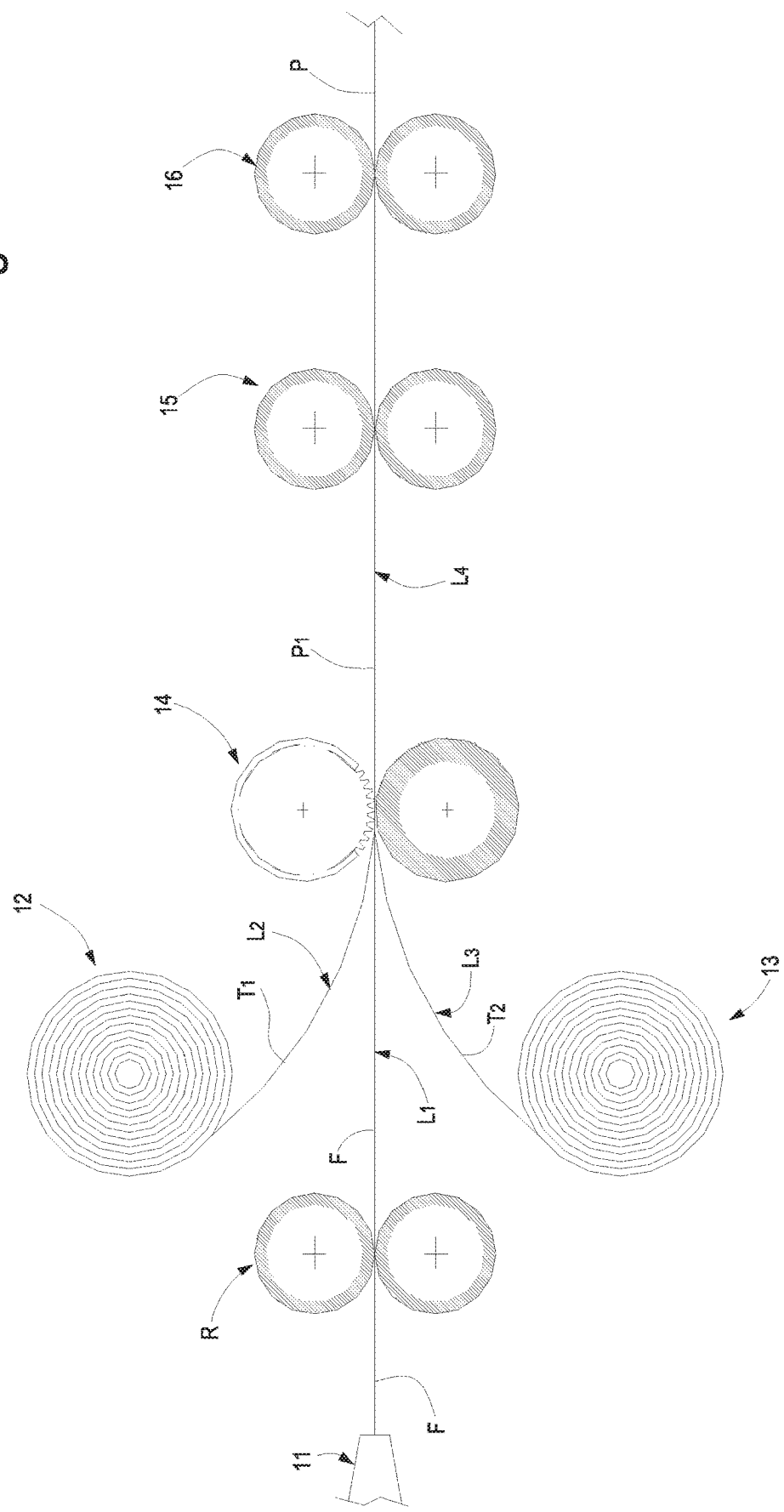
FIG. 1 shows a scheme of a plant for implementing the method according to the invention.

With reference to the previously mentioned figures, number 10 indicates, as a whole, a plant for implementing a production method allowing to produce an elastic laminate especially, but without limitation, suitable for hygienic and sanitary products etc., having high elasticity, high tensile strength and increased softness with respect to known products.

This plant comprises an extruder 11 suitable to coextrude a multi-layer elastic film made of polymer material F.

In this example, the extruder 11 allows the coextrusion of a three-layer film, with the outer layers F1 having the same thickness and being made for example with polyolefin elastomers, for instance Dow® Infuse™, ExxonMobile® Vistamaxx®, and the like, together with polyolefin polymers like poly (ethylene-butene), poly (ethylene-hexene), poly (ethylene-octene), poly (ethylene-propylene) and or polyolefin thermoplastic polymers thereof. The inner layer F2 is made, for example, of one or more of the following materials: block copolymers containing SBS (styrene-butadiene-styrene), SIS (styrene-isoprene-styrene, SEBS (styrene-ethylene-butylene-styrene) and polyolefin elastomers like Dow® Infuse™, ExxonMobile® Vistamaxx®, and the like.

In this example, the inner layer is a combination of SEBS (styrene-ethylene-butylene-styrene) and the outer layers are based on one or more polyethylene polymers.

The film is substantially impermeable and not transpiring. The extruder may have a roller, not shown in the figures, for depositing the film as it exited the extruder mouth.

Downstream of the extruder 11, a cooling station R of the known type is provided, formed, for example, by two cooled rollers, between which the film from the extruder is fed.

The plant also comprises two areas 12 and 13, occupied by accumulations, for instance reels, of nonwoven webs T1 and T2, that in this example have equal dimensions and composition. In this example, the nonwoven webs have bicomponent fibers of the coaxial type. For example, the inner part of the inner coaxial fibers is made of polyethylene, whilst the outer part is made of polypropylene. These nonwovens are preferably spun bound.

The plant 10 furthermore comprises a calender 14 for joining, through spot welding, the web of film F produced by the extruder 11 with two nonwoven webs T1 and T2 coming from the reels 12 and 13.

It should be noted that at least part of the materials forming the outer layers of the elastic film are thermally compatible with at least part of the materials forming the fibers of the nonwoven web they respectively face.

At least one nonwoven web (and preferably both the webs) has a thickness, before entering the calender, comprised between 0.1 mm and 0.6 mm, and more preferably between 0.15 mm and 0.5 mm. In this example, the thickness is equal to 0.199 mm.

Each nonwoven web has a weight, before entering the calender, comprised between 10 g/m² and 40 g/m², and in this example the weight is approximately 20.37 g/m².

The elastic film F has a thickness, before entering the calender 14, comprised for example between 0.04 mm and 0.14 mm, and in this example it is approximately 0.05 mm. The thickness of the inner layer F2 of the film F is comprised between 0.017 mm and 0.075 mm, and in this example it is approximately 0.045 mm. The ratio between the sum of the thicknesses of the two outer layers and the thickness of the inner layer of the coextruded elastic film entering the calender is comprised between 1/3 and 1/25 and more preferably between 1/7 and 1/21. In this example the ratio is 1/9.

The laminate is produced in line. Practically, the production line implemented with the plant 10 has three branches L1, L2, L3, that are respectively for the film web and the two nonwoven webs and join in the calender 14, and a fourth branch L4, exiting from the calender, where the webs F, T1 and T2 are joined together.

According to preferred embodiments, at least part of the materials forming the outer layers of the elastic film are thermally compatible with at least part of the materials forming the fibers of the nonwoven web they respectively face.

Thermal compatibility means the ability of two materials to remain joined together after heat-welding, or to remain joined together when they are thermally fused above each other and then cooled.

Along the line branch L4, downstream of the calender 14, a cooling station 15 is provided for the semi-finished laminated product P1 (formed by the three webs T1, F and T2 joined together through spot welding in the calender), for example of the type with known cooling rollers.

A cross stretching station 16 is provided downstream of the cooling station 15 for stretching the semi-finished laminated product P1 in CD. This cross stretching station 16 is, for example, of the type called "Ring Rolls".

The web exiting from the cross stretching station 16 substantially matches with the elastic laminated product P according to the invention. The elastic laminate may be cut into portions of the desired length, that are wound in reels and stored.

The elastic laminate therefore comprises the polymer intermediate elastic film F formed by the three coextruded layers F1, F2, wherein the outer layers F1 are made of the same polymer material and the inner layer F2 is made of a different polymer material, and by the two nonwovens T1 and T2 joined to the outer faces of the coextruded elastic film F through welding spots or areas Z.

The weight of the laminated product P at the end of processing is comprised between 60 and 140 g/m², and in this example it is approximately 80.2 g/m².

The thickness of the laminated product P at the end of processing is comprised between 0.5 and 0.15 mm, and in this example it is approximately 0.81 mm.

The ratio between MD elongation at break at 10N, and laminate thickness after the stretching step is lower than 8, and preferably lower than 7.5. In this example, it is approximately equal to 6.70.

The ratio in (N/50 mm)/(mm) between CD tensile strength and thickness of the laminate P after the stretching step is lower than 79, and preferably lower than 78. In this example, it is approximately equal to 77.0.

The ratio (in g/m²/mm) between weight and thickness of the laminate P after the stretching step is lower than 105, and more preferably lower than 100. In this example, it is approximately equal to 99.

The welding spot or welding area density is comprised between 15 and 60 spots/cm².

The elastic film F is coextruded by means of the extruder 11. At the end of the coextrusion step, the elastic film has a temperature comprised between 220° C. and 270° C. In this example, it is approximately equal to 250° C.

The film F is fed from the extruder 11 to the calender 14. The temperature of the coextruded elastic film entering the calender after having passed through the cooling station R is comprised between 10° C. and 40° C., more preferably between 15° C. and 35° C., and in this example it is approximately 20° C.

It has been found that, adequately, a given ration between film temperature immediately after extrusion and before the calender allows to obtain high performances in terms of elasticity and strength. The coextruded elastic film F has conveniently a temperature, when entering the calender, equal to, or lower than, 1/7 of the temperature the elastic film has at the end of the coextrusion step; conveniently, this temperature is preferably lower than 1/10.

In order to contribute to the cooling, the first web of coextruded elastic film F may adequately travel, from the extrusion step to the entrance into the calender, an air path whose length is comprised between 5 m and 20 m, and more preferably comprised between 8 m and 13 m; in this example, it is approximately 11 m at average ambient temperature (i.e. the temperature of the place where the production line is arranged).

Also the nonwoven webs T1 and 2 are fed to the calender 11 together with the film F.

The calender 11 has a flat roller 14A and a roller 14B provided with appendices or protuberances, whose vertexes form the welding spots or areas Z.

The temperature of the rollers 14A and 14B of the calender is comprised between 120° C. and 160° C., and in this example it is approximately 140° C. Preferably, the lamination pressure between the calender rollers is comprised between 70 kg/m² and 160 kg/m².

The pressure and the temperature of the calender allows the formation of spots or areas Z where the portions of webs T1 and T1, whose dimensions are similar to those of the protuberances of the roller 14B, are fused with at least corresponding portions of the outer layers F1 of the coextruded elastic film F.

In this example, after having exited the calender, the semi-finished laminated web P1 passes through the cooling station 15. The web P1 is cooled up to a temperature comprised between 15° C. and 40° C., in this example up to approximately 35° C.

After having passed through the cooling station 15, the semi-finished laminated web P1 passes through the mechanical stretching station 16, where it is stretched in CD.

The stretching values are comprised between 150% and 250%, in this example approximately 200%.

Once the laminated web P has been stretched, it can be cut into portions of the desired length, that can be wound and stored.

In order to make the laminated product P functionally transpiring or permeable, it is possible to perform a punching step, preferably between the exit of the calender 11 and the entrance of the stretching station 16, and more preferably after the cooling station, if any. The punching may be, for example, a needle punching. In other examples, the punching may be performed after the stretching step.

The webs T1, T2, P1, and P move substantially continuously during the production step.

It has been found that an important aspect of the present invention is the fact of extruding the elastic film directly in the laminate production line, laminating the extruded film together with the nonwovens. Namely, a comparison has been made (see the following table) between a laminated product directly coextruded in the line, as described above (case A, with the values mentioned above), and a laminated product made by using an elastic film produced in advance, for example one month before, fed for instance from a reel, together with the nonwovens in the calender (case B).

|  | Case A—Laminate with film coextruded in line | Case B—Laminate with previously produced film |
| --- | --- | --- |
| MD elongation at break at 10N (%) | 5.44 | 6.28 |
| CD tensile strength (N/ear-shape) | 63.00 | 60.41 |
| Grammage (g/m$^2$) | 80.2 | 79.6 |
| Thickness (mm) | 0.81 | 0.76 mm |
| Softness (qualitative test) | greater |  | measurements according to EDANA WSP 110.4

Practically, it has been found that producing the coextruded elastic film in line allows a decrease of approximately 13% in the elongation at break at 10N (value of significance for the machinability of the material on the production lines for hygienic sanitary products), an increase of about 4% in CD tensile strength (value of significance during the assembly of diapers; they break less easy), an increase of about 7% in the thickness, and a qualitatively greater softness. It is understood that what illustrated above purely represents possible non-limiting embodiments of the invention, which may vary in forms and arrangements without departing from the scope of the concept on which the invention is based. Any reference numbers in the appended claims are provided for the sole purpose of facilitating the reading thereof in the light of the description before and the accompanying drawings and do not in any way limit the scope of protection of the present invention.

The invention claimed is:

1. A method for production of an elastic laminate, the method comprising the following steps in a same production line:
    coextruding a first web of elastic film to form a coextruded first web of elastic film, said coextruded first web of elastic film comprising at least three layers, said at least three layers comprising at least two different polymer materials;
    contemporaneously feeding said coextruded first web of elastic film and two second nonwoven webs to a thermal binding calender, wherein said coextruded first web of elastic film is arranged between said two second nonwoven webs when entering said thermal binding calender, wherein said first web of elastic film, during movement from a coextrusion step to a thermal binding step, passes from a melted state, in said coextrusion step, to a solidified and cold state when entering said thermal binding calender, wherein said coextruded first web of elastic film has a temperature, when entering said thermal binding calender, equal to, or lower than, one-seventh of said temperature of said first web of elastic film at an end of said coextrusion step;
    joining, through spot welding or area welding in said thermal binding calender, said second nonwoven webs with respective opposite outer layers of said coextruded first web of elastic film to produce an intermediate web; and
    stretching said intermediate web according to a direction transverse to said intermediate web, wherein said intermediate web is cooled to a temperature between 15° C. and 40° C. after the thermal binding step and before the stretching of said intermediate web,
    wherein two outer layers of said coextruded first web of elastic film are made of said same polymer material and have said same thickness.

2. A method according to claim 1, wherein said coextruded first web of elastic film web travels, from said extrusion step to an entrance into said thermal binding calender, an air path comprised between 5 m and 20 m.

3. A method according to claim 1, wherein a ratio between a sum of thicknesses of two outer layers and a thickness of an inner layer of said coextruded first web of elastic film entering said thermal binding calender is between 1/3 and 1/25.

4. A method according to claim 1, wherein at least part of materials forming outer layers of said coextruded first web of elastic film are thermally compatible with at least part of materials of said two second nonwoven webs said outer layers respectively face.

5. A method according to claim 1, wherein at least one of said second nonwoven webs has coaxial bicomponent fibers.

6. A method according to claim 1, wherein at least one of said second nonwoven webs is one of spun-bound, thermobound and spun-laced.

7. A method according to claim 1, wherein at least one of said second nonwoven webs is extendible.

8. A method according to claim 1, wherein at least one of:
    a temperature of rollers of said thermal binding calender is between 120° C. and 160° C.; and
    a lamination pressure between said rollers of said thermal binding calender is between 70 kg/cm and 160 kg/cm.

9. A method according to claim 1, wherein at least one of:
    a ratio between MD elongation at break at 10N, and laminate thickness after stretching said intermediate web is lower than 8;
    a ratio in (N/50 mm)/(mm), between CD tensile strength and laminate thickness after stretching said intermediate web is lower than 79; and
    a ratio in g/m$^2$/mm between laminate weight and thickness after stretching said intermediate web is lower than 105.

10. A method according to claim 1, wherein a density of welding spots or welding areas is between 15 and 60 spots/cm$^2$.

11. A method according to claim 1, wherein said coextruded first web of elastic film has a temperature, when entering said thermal binding calender, equal to, or lower than, one-tenth of said temperature of said first web of elastic film at an end of said coextrusion step.

12. A method according to claim 1, wherein said coextruded first web of elastic film has a temperature between 220° C. and 270° C. at an end of said coextrusion step and said coextruded elastic film has a temperature between 10° C. and 40° C. when entering said thermal binding calender.

13. A method according to claim 1, wherein said coextruded first web of elastic film has a temperature between 220° C. and 270° C. at an end of said coextrusion step, said coextruded first web of elastic film having a temperature between 15° C. and 35° C. when entering said thermal binding calender.

14. A method according to claim 1, wherein said coextruded first web of elastic film web travels, from said extrusion step to an entrance into said thermal binding calender, an air path comprised between 8 m and 13 m.

15. A method according to claim 1, wherein a ratio between a sum of thicknesses of two outer layers and a thickness of an inner layer of said coextruded first web of elastic film entering said thermal binding calender is between 1/7 and 1/21.

16. A method for production of an elastic laminate, the method comprising the following steps in a same production line:
- coextruding a first web of elastic film to form a coextruded first web of elastic film, said coextruded first web of elastic film comprising at least three layers, said at least three layers comprising at least two different polymer materials;
- contemporaneously feeding said coextruded first web of elastic film and two second nonwoven webs to a thermal binding calender, wherein said coextruded first web of elastic film is arranged between said two second nonwoven webs when entering said thermal binding calender, wherein said first web of elastic film, during movement from a coextrusion step to a thermal binding step, passes from a melted state, in said coextrusion step, to a solidified and cold state when entering said thermal binding calender, wherein said coextruded first web of elastic film has a temperature, when entering said thermal binding calender, equal to, or lower than, one-seventh of said temperature of said first web of elastic film at an end of said coextrusion step;
- joining, through spot welding or area welding in said thermal binding calender, said second nonwoven webs with respective opposite outer layers of said coextruded first web of elastic film to produce an intermediate web; and
- stretching said intermediate web according to a direction transverse to said intermediate web, wherein said intermediate web is cooled to a temperature between 15° C. and 40° C. after the thermal binding step and before the stretching of said intermediate web,
- wherein a thickness of a laminated web exiting said production line has an increased thickness with respect to a sum of said second nonwoven webs and said coextruded first web of elastic film entering said thermal binding calender,
- wherein said increased thickness is between 50% and 66% of said sum of said second nonwoven webs and said coextruded first web of elastic film before entering said thermal binding calender.

* * * * *